US010471111B2

(12) United States Patent
Kim et al.

(10) Patent No.: US 10,471,111 B2
(45) Date of Patent: Nov. 12, 2019

(54) LACTOBACILLUS AND COMPOSITION FOR PREVENTING, IMPROVING, OR TREATING DEGENERATIVE BRAIN DISEASES OR COGNITIVE FUNCTION DISORDERS

(71) Applicant: University-Industry Cooperation Group of Kyung Hee University, Yongin-si, Gyeonggi-do (KR)

(72) Inventors: Dong Hyun Kim, Seoul (KR); Myung Joo Han, Seoul (KR)

(73) Assignee: University-Industry Cooperation Group of Kyung Hee University (KR)

( * ) Notice: Subject to any disclaimer, the term of this patent is extended or adjusted under 35 U.S.C. 154(b) by 0 days.

(21) Appl. No.: 15/759,928

(22) PCT Filed: Sep. 6, 2016

(86) PCT No.: PCT/KR2016/009961
§ 371 (c)(1),
(2) Date: Mar. 14, 2018

(87) PCT Pub. No.: WO2017/047962
PCT Pub. Date: Mar. 23, 2017

(65) Prior Publication Data
US 2018/0355445 A1    Dec. 13, 2018

(30) Foreign Application Priority Data

Sep. 15, 2015  (KR) .................. 10-2015-0130124
Jan. 6, 2016  (KR) .................. 10-2016-0001312

(51) Int. Cl.
| | | |
|---|---|---|
| A61K 35/747 | (2015.01) |
| C12R 1/25 | (2006.01) |
| A61K 35/745 | (2015.01) |
| A61P 25/28 | (2006.01) |
| C12R 1/225 | (2006.01) |
| A61K 35/00 | (2006.01) |
| A23L 33/135 | (2016.01) |
| A61K 36/48 | (2006.01) |

(52) U.S. Cl.
CPC .......... A61K 35/747 (2013.01); A23L 33/135 (2016.08); A61K 35/745 (2013.01); A61K 36/48 (2013.01); A61P 25/28 (2018.01); C12R 1/225 (2013.01); C12R 1/25 (2013.01); *A23V 2002/00* (2013.01); *A23Y 2220/43* (2013.01); *A23Y 2220/67* (2013.01); *A61K 2035/115* (2013.01)

(58) Field of Classification Search
CPC ....... C12R 1/225; A61P 25/28; A61K 35/747; A23L 33/135; A23V 2002/00; A23Y 2220/43

See application file for complete search history.

(56) References Cited

U.S. PATENT DOCUMENTS

| | | | |
|---|---|---|---|
| 9,603,878 B2 * | 3/2017 | Berry | .................. A61K 9/0031 |
| 9,801,915 B2 | 10/2017 | Bel-Rhlid et al. | |
| 1,002,898 A1 | 7/2018 | Yamamoto et al. | |
| 2011/0046235 A1 | 2/2011 | Bel-Rhlid et al. | |
| 2015/0174177 A1 | 6/2015 | Bel-Rhlid et al. | |
| 2015/0306158 A1 | 10/2015 | Kim et al. | |
| 2016/0000841 A1 | 1/2016 | Yamamoto et al. | |
| 2017/0368114 A1 | 12/2017 | Kim et al. | |
| 2018/0028582 A1 | 2/2018 | Bel-Rhlid et al. | |

FOREIGN PATENT DOCUMENTS

| | | | | |
|---|---|---|---|---|
| JP | 2011-518570 | | 6/2011 | |
| JP | 2012-136436 | | 7/2012 | |
| JP | 2012136436 | * | 7/2012 | ............... A23L 1/30 |
| JP | 2015-526085 | | 9/2015 | |
| JP | 2015-521613 | | 7/2016 | |
| KR | 10-1087972 | | 12/2011 | |
| KR | 10-1424547 | | 8/2014 | |
| KR | 10-1476236 | | 12/2014 | |
| KR | 2015-0047687 | | 5/2015 | |
| KR | 2016-0101660 | | 8/2016 | |
| WO | 2013/190068 | | 12/2013 | |
| WO | WO-2013190068 A1 * | 12/2013 | ........... A61K 31/216 |
| WO | WO 2014/130540 | | 8/2014 | |
| WO | WO2017047962 A1 | | 3/2017 | |

OTHER PUBLICATIONS

Lim et al., Lactobacillus johnsonii CJLJ103 attenuates colitis and memory impairment in mice by inhibiting gut microbiota lipopolysaccharide production and NF-kB activation. J. Functional Foods., 2017, vol. 34: 359-368. (Year: 2017).*

Wen et al., Innate immunity and intestinal microbiota in the development of of type 1 diabetes. Nature., 2008, vol. 455: 1109-1113 (Year: 2008).*

Agerholm-Larsen et al., *The effect of a probiotic milk product on plasma cholesterol: a meta-analysis of short-term intervention studies*, Eur J Clin Nutr, 54(11):856-860 (2000).

Hivak et al., *One-year application of probiotic strain Enterococcus faecium M-74 decreases serum cholesterol levels*, Bratisl Lek Listy, 106(2):67-72 (2005).

(Continued)

*Primary Examiner* — Ganapathirama Raghu
(74) *Attorney, Agent, or Firm* — Fish & Richardson P.C.

(57) ABSTRACT

The present invention provides a novel *lactobacillus* and a use for same, the *lactobacillus* being separated from kimchi and thus highly safe, and having various types of biological activity such as memory improving activity, tight junction protein expression inducing activity, antioxidation activity, lipopolysaccharide (LPS) generation-suppressing activity, and β-glucuronidase inhibiting activity. The novel *lactobacillus* according to the present invention may be used as a functional food medicine material for preventing, improving, or treating degenerative brain diseases or cognitive function disorders.

8 Claims, 2 Drawing Sheets

Specification includes a Sequence Listing.

(56) References Cited

OTHER PUBLICATIONS

Lukacova et al., *In vitro testing of selected probiotic characteristics of Lactobacillus plantarum and Bifidobacterium longum* Journal of Food and Nutrition Research, 45:77-83 (2006).

Pridmore et al., *The genome sequence of the probiotic intestinal bacterium Lactobacillus johnsonii NCC 533* Proc Natl Acad Sci USA. 101(8):2512-7 (2004).

Sarter, et al., *Attenuation of scopolamine-induced impairment of spontaneous alteration behaviour by antagonist but not inverse agonist and agonist beta-carbolines*, Psychopharmacology, 94(4):491-495 (1988).

Sousa et al., *Effect of Lactobacillus acidophilus supernatants on body weight and leptin expression in rats*; BMC complementary and alternative medicine, 8(5):1-8 (2008).

Suriasih et al., *Microbiological and Chemical Properties of Kefir Made of Bali Cattle Milk*, Food Science and Quality Management 6:112-22 (2012).

Tannock, Gerald W., et al., "Resource Partitioning in Relation to Cohabitation of *Lactobacillus* Species in the Mouse Forestomach," The I.S.M.E. Journal [electronic publishing] Nov. 17, 2011, vol. 6, No. 5, pp. 927-938.

Liu, Hao-Yu et al., "effects of Lactobacilus Johnsonii and Lactobacillus Reuteri on Gut Barrier Function and Heat Shock Proteins in Intestinal Porcine Epithelial Cells," Physiological Reports, Apr. 2015, vol. 3, No. 4, p. e12355.

NCBI, GenBank Accession No. M99704.1, Sep. 7, 1993.

ISR/KR, International Search Report for PCT/KR2016/009961 (dated Jan. 9, 2017).

NZ Patent Office, First Examination Report dated Aug. 24, 2018 (5 pages).

Jhan, et al, Production of fermented red beans with multiple bioactivities using co-cultures of *Bacillus subtilis* and *Lactobacillus delbrueckii* subsp. *bulgaricus*, LWT—Food Science and Technology, 63(2):1281-1287 (Apr. 2015).

Liao, et al, Influence of preprocessing methods and fermentation of adzuki beans on y-aminobutyric acid (GABA) accumulation by lactic acid bacteria, Journal of Functional Foods, 5(3):1108-1115 (Jun. 2013).

Lim et al, Lactobacillus johnsonii CJLJ103 attenuates colitis and memory impairment in mice by inhibiting gut microbiota lipopolysaccharide production and NF-KB activation, Journal of Functional Foods, (May 2017) (Abstract) (3 pages).

EP Extended Search Report for App No. EP 16846783.5 dated Mar. 29, 2019 (10 pages).

Gan et al., Fermentation alters antioxidant capacity and polyphenol distribution in selected edible legumes, International Journal of Food Science and Technology, 51:875-884 (2016).

Jaspers et al., Ecological Significance of Microdiversity: Identical 16S rRNA Gene Sequences Can Be Found in Bacteria with Highly Divergent Genomes and Ecophysiologies, App and Environ Microbiology, 70(8): 4831-4839, Aug. 2004.

JP Office Action for App No. JP 2018-513764, dated Apr. 2, 2019 (with English translation) (7 pages).

Kamitani et al., Functional Investigation of Sweet Red Bean Pastes as Anti-oxidant Food: Polyphenol Contents, Superoxide Dismutase Activity, and Inhibitory Effects on Reactive Oxygen Species, Japanese Society for Food Science and Technology, 62(7):349-353 (2015).

\* cited by examiner

LACTOBACILLUS AND COMPOSITION FOR PREVENTING, IMPROVING, OR TREATING DEGENERATIVE BRAIN DISEASES OR COGNITIVE FUNCTION DISORDERS

SEQUENCE LISTING

The instant application contains a Sequence Listing which has been submitted electronically in ASCII format and is hereby incorporated by reference in its entirety. Said ASCII copy, created on Jul. 25, 2018, is named 46533-0002US1.txt and is 5,815 bytes in size.

TECHNICAL FIELD

The present invention relates to novel lactic acid bacteria and the use thereof, and more particularly to novel lactic acid bacteria, which is isolated from Kimchi, having various types of physiological activities, such as memory improvement activity, tight junction protein expression inducement activity, antioxidant activity, lipopolysaccharide (LPS) production-inhibitory activity or β-glucuronidase-inhibitory activity, and to food and medicinal uses of novel lactic acid bacteria for preventing, alleviating or treating degenerative brain diseases or cognitive function disorders.

BACKGROUND ART

With the rise of aging society, the number of patients with degenerative brain diseases, such as Alzheimer's disease, Parkinson's disease and dementia is rapidly increasing. Alzheimer's disease, the most common degenerative brain disease that causes dementia, slowly develops and gradually deteriorates cognitive functions including memory. While the exact cause of Alzheimer's disease has yet to be found, it is closely associated with aging and is growing with the increase of the older population.

Parkinson's disease is a chronic progressive degenerative disease of the nerve system caused by the loss of dopamine neurons, showing symptoms of muscle cramps, bradykinesia (slowness of movement) and postural instability. Patients with Alzheimer's disease show symptoms of dementia, such as speech impairment and executive function inability while patients with Parkinson's disease show symptoms of dementia, such as lapses in concentration and visual/spatial judgment, executive function disorder and slowness in thinking.

Dementia may be defined as a condition where a physically stable person experiences damage to brain function due to various causes and gradual deterioration of the overall cognitive ability, greatly affecting daily life activities. Cognitive ability herein means various intellectual abilities, such as memory, speech, visual-spatial ability, judgment and abstract thinking. Each of the cognitive abilities is deeply associated with a certain part of brain. About 50% of dementia are a Alzheimer's disease-type, 20 to 30% of dementia are a blood vessel-type and there are other types of dementia, such as alcohol-related dementia, dementia with Lewy bodies, frontotemporal dementia, and Parkinson's disease dementia. Recently, there have been studies that various degenerative brain diseases including dementia are associated with Intestinal Permeability Syndrome or intestinal flora disturbance.

Intestinal Permeability Syndrome and Dementia

The gastrointestinal tract of the human body is composed of mucus and villi, which efficiently absorb nutrient components, but prevent the absorption of pathogenic microorganisms having a high molecular weight or toxins produced by these microorganisms. In addition, the human body has an immune system capable of protecting the body from invasion of external antigens having a high molecular weight. However, due to infection with many pathogenic microorganisms or toxins, excessive stress, intake of foods such as high-fat diets capable of proliferating harmful bacterial living in the gastrointestinal tract, excessive alcohol intake, the abuse of drugs (e.g., antibiotics) and the like, intestinal flora is disturbed, abnormalities in the gastrointestinal tract's immune system occur, and expression of tight junction proteins is inhibited. If expression of tight junction proteins is inhibited, tight junction of intestinal mucosa becomes loosened, and the invasion into the body of large molecules due to the loosened gap and abnormalities in the immune system. Intestinal permeability syndrome is also known as leaky gut syndrome, and refers to a condition in which external such as less digested foods, pathogenic microorganisms, toxins or the like are continuously introduced into blood, because the tight junction barrier system of epithelial cells forming the gastrointestinal tract is not smoothly operated. When intestinal permeability syndrome occurs, external antigens that are generally not absorbed into the body enter the body, thus causing ulcerative colitis, Crohn's disease, liver injury, liver dysfunction, allergic diseases (including asthma), atopy, autoimmune diseases, steatorrhea, digestive absorption disorder, acne, accelerated aging, endotoxemia, intestinal infection, eczema, irritable bowel syndrome, chronic fatigue syndrome, psoriasis, rheumatoid arthritis, pancreatic insufficiency, inflammatory joint diseases or the like. Recently, there have been studies that Intestinal Permeability Syndrome is associated with dementia caused by Parkinson's disease or aging.

Intestinal Flora Disturbance and Dementia

There are many bacteria living in the gastrointestinal tract of the human body. The human body has about 10 trillion normal cells, but has about 100 trillion bacteria which are about 10-fold larger than the normal cells. These bacteria may be divided into beneficial bacteria that help human intestinal health and harmful bacteria that are harmful to human health. The health of human body may be maintained when beneficial bacterial such as *Lactobacillus, Bifidobacterium, Streptococcus, Leuconostoc, Pediococcus, Sporolactobacillius* and the like are more dominant in the gastrointestinal tract than harmful bacteria. Otherwise, diseases may be caused, such as obesity, intestinal permeability syndrome, liver diseases, accelerated aging, enteritis, accelerated aging, dementia and the like. Increase of harmful microorganisms in the intestinal flora (ex. *Klebsiella pneumoniae, Escherichia coli, Proteus mirabilis*, etc.) boosts the activity of NF-kB in intestinal cells, which can dramatically increase the possibility of degenerative brain diseases, such as Alzheimer's disease and Parkinson's disease, and dementia.

Probiotics are collectively referred to as live microorganisms that improve the host's microbial environment in the gastrointestinal tract of animals, including humans, and have beneficial effects on the host's health. In order to be effective as probiotics, it is necessary to have excellent acid resistance, bile resistance and adherence to epithelial cells, because most of these probiotics should reach the small intestine upon oral administration and must be adhered to the intestinal surface. Lactic acid bacteria are used as probiotics because they play a role in decomposing fibrous and complex proteins to make important nutrients while living in the digestive system of the human body. Lactic acid bacteria have been reported to exhibit effects such as maintenance of intestinal normal flora, improvement of intestinal flora, anti-diabetic and anti-hyperlipidemic effects, inhibition of carcinogenesis, inhibition of colitis, and nonspecific activity of the host's immune system. Among these lactic acid bacteria, *Lactobacillus* sp. strains are major members of normal microbial communities living in the bowel of the human body and have long been known to be important in maintaining a healthy digestive tract and vaginal environment. Currently, according to the U.S. Public Health Service guidelines, all the *Lactobacillus* strains deposited with the American Type Culture Collection (ATCC) are classified as 'Bio-Safety Level 1', which is recognized as having no known potential risk of causing disease in humans or animals. Meanwhile, lactic acid bacteria of kimchi that are involved in kimchi fermentation have been reported to have immune enhancement effects, antimicrobial effects, antioxidant effects, anti-cancer effects, anti-obesity effects, hypertension preventive effects or constipation preventive effects [Hivak P, Odrska J, Ferencik M, Ebringer L, Jahnova E, Mikes Z. One-year application of Probiotic strain *Enterococcus facium* M-74 decreases Serum cholesterol levels: Bratisl lek Listy 2005; 106(2); 67-72; Agerholm-Larsen L. Bell M L. Grunwald G K. Astrup A.: The effect of a probiotic milk product on plasma cholesterol: a metaanalysis of short-term intervention studies; Eur J Clin Nutr. 2000; 54(11) 856-860; Renato Sousa, Jaroslava Helper, Jian Zhang, Strephen J Lewis and Wani O Li; Effect of *Lactobacillus acidophilus* supernants on body weight and leptin expression in rats; BMC complementary and alternative medicine. 2008; 8(5)1-8].

Since various bioactive activities of lactic acid bacteria were known, There have recently been a growing number of studies designed to develop a safe and highly functional lactic acid bacteria flora for the human body and turn it into an ingredient of medicinal products or functional foods. For example, the Korean Patent Gazette for registration No. 10-1476236 discloses a pharmaceutical composition for prevention or treatment of dementia, comprising *lactobacillus pentosus* var. *plantarum* C29 KCCM11291P flora as an active ingredient. The Korean Patent Gazette for registration No. 10-1087972 discloses the preparation method of lactic acid bacteria ferment that is effective in preventing and treating dementia, comprising (a) a stage to inoculate, culture and ferment lactic acid bacteria selected from *lactobacillus* sp., *enterococcus* sp. and *bifidobacterium* sp. into the medium comprising milk; (b) a stage to remove lactic acid bacteria from the above ferment; and (c) a stage to precipitate separate active ingredients adding a solvent selected from a group consisting of acetone and alcohol having 1 to 6 carbon atoms to the ferment, which had lactic acid bacteria removed. In addition, the Korean Patent Gazette for registration No. 10-1424547 discloses a pharmaceutical composition for preventing or treating degenerative brain diseases comprising the lactic acid bacteria ferment of *Lactobacillus fermentum* KFRI 164 of Sibjeondaebotang, as an active ingredient. Also, the Korean Patent Gazette for publication No. 10-2015-0047687 discloses a composition for preventing or improving forgetfulness or improving memory, comprising the plant extract that was fermented by adding 0.1 to 10 wt % of glucose and 0.1 to 5 wt % of yeast extract to a plant extract, hot-water extracted from *Polygala tenuifolia*, white *Poria cocos* Wolf, and *Acoris gramineus*, and then inoculating the cultured *Lactobacillus plantarum*.

And yet, lactic acid bacteria disclosed in the prior art or the product fermented by the same is not enough to be applied as a commercial treatment since it is not highly effective in treating degenerative brain diseases including dementia. As such, it is necessary to screening a certain type of lactic acid bacteria that has the equivalent level of treatment effect for brain diseases compared to commercial treatments, and improves Intestinal Flora Disturbance and Intestinal Permeability Syndrome, thereby developing medicinal products or functional foods.

DISCLOSURE

Technical Problem

The present invention has been made under the Background Art as described above, and it is an object of the present invention to provide novel lactic acid bacteria having various physiological activities or functionalities required for probiotics.

In addition, an object of the present invention is to provide a composition that comprises novel lactic acid bacteria or ferment thereof and may be used to alleviate, prevent or treat degenerative brain diseases.

Technical Solution

To achieve the above objects, an embodiment of the present invention is *Lactobacillus johnsonii* comprising 16S rDNA nucleotide sequence represented by SEQ ID NO: 2, which provides the lactic acid bacteria having the memory improvement activity, tight junction protein expression inducement activity, antioxidant activity, lipopolysaccharide (LPS) production inhibitory activity or β-glucuronidase inhibitory activity.

To achieve the above objects, an embodiment of the present invention provides a pharmaceutical composition for preventing or treating degenerative brain diseases or cognitive function disorder comprising a lactic acid bacteria corresponding to *Lactobacillus johnsonii* comprising a 16S rDNA nucleotide sequence represented by SEQ ID NO: 2, a culture of the lactic acid bacteria, a lysate of the lactic acid bacteria or an extract of the lactic acid bacteria as an active ingredient. Still another embodiment of the present invention provides a food composition for preventing or alleviating degenerative brain diseases or cognitive function disorder comprising a lactic acid bacteria corresponding to *Lactobacillus johnsonii* comprising a 16S rDNA nucleotide sequence represented by SEQ ID NO: 2, a culture of the lactic acid bacteria, a lysate of the lactic acid bacteria or an extract of the lactic acid bacteria as an active ingredient. Still another embodiment of the present invention provides a food composition for improving memory or learning ability comprising a lactic acid bacteria corresponding to *Lactobacillus johnsonii* comprising a 16S rDNA nucleotide sequence represented by SEQ ID NO: 2, a culture of the lactic acid bacteria, a lysate of the lactic acid bacteria or an extract of the lactic acid bacteria as an active ingredient.

To achieve the above objects, another embodiment of the present invention provides a pharmaceutical composition for preventing or treating degenerative brain diseases or cognitive disorder, comprising red bean ferment or extract of the red bean ferment as an active ingredient. Also, another embodiment of the present invention provides a food composition for preventing or alleviating degenerative brain diseases or cognitive function disorder, comprising red bean ferment or extract from the red bean ferment. In addition, another embodiment of the present invention provides a food composition for improving memory or learning ability, comprising red bean ferment or extract from the red bean ferment. In the composition according to another embodiment of the present invention, the above red bean ferment is a product that was fermented with lactic acid bacteria that comprises 16S rDNA nucleotide sequence represented by SEQ ID NO: 2 and corresponds to *Lactobacillus johnsonii*.

Advantageous Effects

A certain *Lactobacillus* sp. strain according to the present invention is isolated from kimchi, and thus is highly safe, and has various physiological activities such as memory improvement activity, tight junction protein expression inducement activity, antioxidant activity, lipopolysaccharide (LPS) production inhibitory activity or β-glucuronidase inhibitory activity. Accordingly, a certain *Lactobacillus* sp. strain according to the present invention may be used as an ingredient of medicinal products or functional foods for preventing, alleviating or treating various diseases through combination of the strain's first effect that alleviates intestinal permeability and the secondary effect that improves learning ability or memory.

MODE FOR INVENTION

Figure 1:
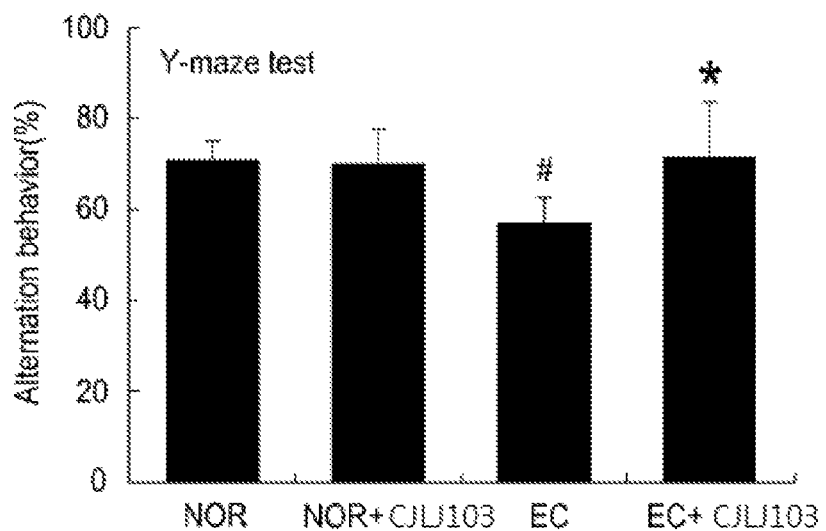
FIG. 1 is a graph showing the impact that administration of *Lactobacillus johnsonii* CJLJ103 has on the Y-maze test of model animals induced to have memory impairment by *Escherichia coli* K20.

As used herein, terms used in the present invention will be defined.

As used herein, the term "cognitive function disorder" means a symptom or disease where cognitive functions, such as memory-processing, cognition or problem-solving do not fully function, specifically including declining working memory, attention and vigilance, linguistic learning and memory, visual learning and memory, and reasoning and problem-solving, namely, executive function, processing speed or social cognition.

As used herein, the term "brain disease" means all types of diseases generated in the brain due to destroyed cranial nerve cells.

As used herein, the term "culture" means a product obtained by culturing a microorganism in a known liquid medium or solid medium, and thus is intended to include a microorganism.

As used herein, the term "ferment" means a product yielded by fermenting the raw ingredient, a subject of fermentation, with microorganism, and a concept comprising microorganism.

As used herein, the term "lactic acid bacteria, etc." means lactic acid bacteria, and culture, lysate or extract of the lactic acid bacteria.

As used herein, the term "red bean ferment, etc." means the red bean ferment or extract of the ferment.

As used herein, the terms "pharmaceutically acceptable" and "sitologically acceptable" means neither significantly stimulating an organism nor inhibiting the biological activity and characteristics of an active material administered.

As used herein, the term "preventing" refers to all actions that inhibit symptoms or delay the progression of a particular disease by administrating the composition of the present invention.

As used herein, the term "treating" refers to all actions that alleviate or beneficially change the symptoms of a particular disease by administering the composition of the present invention.

As used herein, the term "alleviating" refers to all actions that at least reduce a parameter related to the condition to be treated, for example, the degree of symptom.

As used herein, the term "administering" means providing the composition of the present invention to a subject by any suitable method. As used herein, the term "subject" means all animals, including humans, monkeys, dogs, goats, pigs or rats, which have a particular disease whose symptoms may be alleviated by administering the composition of the present invention.

As used herein, the term "pharmaceutically effective amount" refers to an amount sufficient to treat diseases, at a reasonable benefit/risk ratio applicable to any medical treatment. The pharmaceutically effective amount may be determined depending on factors including the kind of subject's disease, the severity of the disease, the activity of the drug, sensitivity to the drug, the time of administration, the route of administration, excretion rate, the duration of treatment and drugs used in combination with the composition, and other factors known in the medical field.

Hereinafter, the present invention will be described in detail.

One aspect of the present invention is related to novel lactic acid bacteria having various physiological activities.

A lactic acid bacteria according to one embodiment of the present invention is *Lactobacillus johnsonii* comprising 16S rDNA nucleotide sequence represented by SEQ ID NO: 2, having memory improvement activity, tight junction protein expression inducement activity, antioxidant activity, lipopolysaccharide (LPS) production inhibitory activity or β-glucuronidase inhibitory activity. The *Lactobacillus johnsonii* is an anaerobic *bacillus* isolated from kimchi, is positive to gram staining, can survive in a wide temperature range and low pHs, and produces glucosidase. Furthermore, the *Lactobacillus johnsonii* utilizes D-glucose, D-fructose, D-mannose, N-acetyl-glucosamine, maltose, lactose, sucrose, gentibiose and the like as carbon sources. In addition, the *Lactobacillus johnsonii* is preferably *Lactobacillus johnsonii* CJLJ103 (accession number: KCCM 11763P).

One aspect of the present invention relates to a composition comprising a particular lactic acid bacteria, etc., as an active ingredient. The composition according to one embodiment of the present invention comprises 16S rDNA nucleotide sequence represented by SEQ ID NO: 2, and also comprises lactic acid bacteria corresponding to *Lactobacillus johnsonii*, culture, lysate or extract thereof as an active ingredient. The *Lactobacillus johnsonii*, is an anaerobic *bacillus* isolated from kimchi and positive to gram staining, and survives in a wide range of temperatures with low PH environment and produces glucosidase. Also, the *Lactobacillus johnsonii* uses D-glucose, D-fructose, D-mannose, N-acetyl-glucosamine, Maltose, Lactose, Sucrose, Gentiobiose and the like as a carbon source. In addition, the *Lactobacillus johnsonii* is preferably *Lactobacillus johnsonii* CJLJ103 (accession number: KCCM 11763P).

In the present invention, a culture of the lactic acid bacteria is a produced by culturing a certain strain or a mixture of strains in a medium. The medium may be selected from known liquid media or solid media, and may be, for example, MRS liquid medium, MRS agar medium or BL agar medium.

The composition according to one embodiment of the present invention may be used to prevent, alleviate or treat degenerative brain diseases or cognitive function disorder, since lactic acid bacteria, etc., the active ingredient, has various types of physiological activities, such as memory improvement activity, tight junction protein expression inducement activity, antioxidant activity, lipopolysaccharide (LPS) production inhibitory activity or β-glucuronidase inhibitory activity. The degenerative brain disease may be Alzheimer's disease, Parkinson's disease, Huntington's disease, or dementia, specifically. Also, the dementia may be selected from a group consists of senile dementia, vascular dementia, Lewy body dementia, frontotemporal dementia, Alzheimer's disease-type dementia, Parkinson's disease-type dementia, Huntington's disease-type dementia, Creutzfeldt-Jacob disease-type dementia, Pick's disease-type dementia, normal pressure hydrocephalus-causing dementia and head injury-causing dementia. Also, the composition according to one embodiment of the present invention may be used to improve memory or learning ability.

Another aspect of the present invention relates to a composition comprising a product fermented by lactic acid bacteria, etc., as an active ingredient. The composition according to another embodiment of the present invention comprises red bean ferment or extract of the same. In the composition according to another embodiment of the present invention, the red bean ferment is a product that the red bean was fermented with lactic acid bacteria corresponding to *Lactobacillus johnsonii* and comprising 16S rDNA nucleotide sequence represented by SEQ ID NO: 2. In the composition according to another embodiment of the present invention, the technical characteristics of the *Lactobacillus johnsonii* are as described above, and thus the description thereof is omitted.

Red bean ferment, an active ingredient of the composition according to another embodiment of the present invention, has higher physiological activity than lactic acid bacteria and is more effective in the aspect of functional food and medicinal ingredient, since the ferment comprises both the secondary metabolite produced by the red bean fermentation and lactic acid bacteria used in the red bean fermentation. The composition according to another embodiment of the present invention may be used to prevent, alleviate or treat degenerative brain diseases or cognitive function disorder. The degenerative brain diseases may be Alzheimer's disease, Parkinson's disease, Huntington's disease, or dementia, specifically. Also, the dementias may be selected from a group consists of senile dementia, vascular dementia, Lewy body dementia, frontotemporal dementia, Alzheimer's disease-type dementia, Parkinson's disease-type dementia, Huntington's disease-type dementia, Creutzfeldt-Jacob disease-type dementia, Pick's disease-type dementia, normal pressure hydrocephalus-causing dementia and head injury-causing dementia. Also, the composition according to another embodiment of the present invention may be used to improve memory or learning ability.

In the present invention, the composition may be embodied as a pharmaceutical composition, a food additive, a food composition (particularly, a functional food composition), a feed additive or the like depending on the intended use or aspect. In addition, the content of the lactic acid bacteria, etc. or red bean ferment, etc., as an active ingredient may also be adjusted within a wide range depending on the specific type, intended use or aspect of the composition.

The content of the lactic acid bacteria, etc. or red bean ferment, etc., as an active ingredient in the pharmaceutical composition according to the present invention is not particularly limited. For example, the content may be 0.01 to 99 wt %, preferably 0.5 to 50 wt %, more preferably 1 to 30 wt %, based on the total weight of the composition. In addition, the pharmaceutical composition according to the present invention may further contain, in addition to the active ingredient, additives such as pharmaceutically acceptable carriers, excipients or diluents. Carriers, excipients and diluents, which may be contained in the pharmaceutical composition according to the present invention, include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate and mineral oil. In addition, the pharmaceutical composition according to the present invention may further contain, in addition to the lactic acid bacteria, etc. or red bean ferment, etc., one or more active ingredients having the effect of preventing or treating degenerative brain diseases or cognitive function disorder. The pharmaceutical composition according to the present invention may be prepared as formulations for oral administration or formulations for parenteral administration, and the formulations may be prepared using diluents or excipients, such as fillers, extenders, binders, wetting agents, disintegrants, surfactants and the like, which are commonly used. Solid formulations for oral administration include tablets, pellets, powders, granules, capsules and the like, and such solid formulations may be prepared by mixing the active ingredient with at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics, preservatives and the like, in addition to water and liquid paraffin which are frequently used simple diluents. Formulations for parenteral administration include sterilized aqueous solutions, non-aqueous solutions, suspensions, emulsions, freeze-dried preparations and suppositories. Propylene glycol, polyethylene glycol, plant oils such as olive oil, injectable esters such as ethyl oleate and the like may be used as non-aqueous solvents or suspending agents. As the base of the suppositories, witepsol, Macrogol, Tween 61, cacao butter, laurin fat, glycerogelatin and the like may be used. Furthermore, the composition may preferably be formulated depending on each disease or component by a suitable method known in the art or the method disclosed in Remington's Pharmaceutical Science (the latest edition), Mack Publishing Company, Easton Pa. The pharmaceutical composition of the present invention may be administered orally or parenterally to mammals, including humans, according to a desired method. Routes for parenteral administration include skin external application, intraperitoneal injection, intrarectal injection, subcutaneous injection, intravenous injection, intramuscular injection, intrathoracic injection or the like. The dose of the pharmaceutical composition of the present invention is not particularly limited as long as it is a pharmaceutically effective amount. The dose may vary depending on the patient's weight, age, sex, health condition, diet, administration time, administration mode, excretion rate and the severity of the disease. The daily dose of the pharmaceutical composition of the present invention is not particularly limited, but is preferably 0.1 to 3000 mg/kg based on an active ingredient, more preferably 1 to 2000 mg/kg based on an active ingredient and may be administered once or several times a day.

Furthermore, the content of the lactic acid bacteria, etc. or red bean ferment, etc., as an active ingredient in the food composition according to the present invention is 0.01 to 99 wt o, preferably 0.1 to 50 wt o, more preferably 0.5 to 25 wt o, based on the total weight of the composition, but is not limited thereto. The food composition of the present invention may be in the form of pellets, powders, granules, infusions, tablets, capsules, liquid or the like, and specific examples of the food may include meats, sausages, breads, chocolates, candies, snacks, confectionaries, pizzas, ramens, other noodles, gums, dairy products including ice creams, various kinds of soups, beverages, teas, functional water, drinks, alcoholic beverages, vitamin complexes and the like, and may include all health foods in a general sense. The food composition of the present invention may further contain sitologically acceptable carriers, various flavoring agents or natural carbohydrates as additional ingredients, in addition to the active ingredient. Additionally, the food composition of the present invention may contain various nutrients, vitamins, electrolytes, flavoring agents, coloring agents, pectic acid and its salt, alginic acid and its salt, an organic acid, a protective colloidal thickener, a pH adjusting agent, a stabilizer, a preservative, glycerin, alcohol, a carbonating agent used for carbonated drinks and the like. Additionally, the food composition of the present invention may contain fruit flesh for preparing natural fruit juices, fruit juice drinks and vegetable drinks. These ingredients may be used independently or as a mixture. The above-described natural carbohydrates may include monosaccharides such as glucose and fructose, disaccharides such as maltose and sucrose, polysaccharides such as dextrin and cyclodextrin and sugar alcohols such as xylitol, sorbitol, and erythritol. As a flavoring agent, a natural flavoring agent such as thaumatin or a stevia extract, or a synthetic flavoring agent such as saccharin or aspartame may be used.

Hereinafter, the present invention will be described in further detail with reference to examples. It is to be understood, however, that these examples are merely intended to clearly illustrate the technical characteristics of the present invention and do not limit the scope of the present invention.

1. Isolation and Identification of Lactic Acid Bacteria (1) Isolation of Lactic Acid Bacteria from Kimchi Each of Chinese cabbage kimchi, radish kimchi and green onion kimchi was crushed, and the crushed liquid was suspended in MRS liquid medium (MRS Broth; Difco, USA). Next, the supernatant was collected, transferred to MRS agar medium (Difco, USA) and cultured anaerobically at 37° C. for about 48 hours, and then strains that formed colonies were isolated.

(2) Isolation of Lactic Acid Bacteria from Human Feces

Human feces were suspended in GAM liquid medium (GAM broth; Nissui Pharmaceutical, Japan). Next, the supernatant was collected, transferred to BL agar medium (Nissui Pharmaceutical, Japan) and cultured anaerobically at 37° C. for about 48 hours, and then *Bifidobacterium* sp. strains that formed colonies were isolated.

(3) Identification of Screened Lactic Acid Bacteria

The physiological characteristics and 16S rDNA sequences of the strains isolated from kimchi or human feces were analyzed to identify the species of the strains, and names were given to the strains. Table 1 below the control numbers and strain names of the lactic acid bacteria isolated from Chinese cabbage kimchi, radish kimchi, green onion kimchi and human feces.

TABLE 1

| Control No. | Strain name |
|---|---|
| 1 | Lactobacillus acidophilus CH1 |
| 2 | Lactobacillus acidophilus CH2 |
| 3 | Lactobacillus acidophilus CH3 |
| 4 | Lactobacillus brevis CH4 |
| 5 | Lactobacillus curvatus CH5 |
| 6 | Lactobacillus brevis CH6 |
| 7 | Lactobacillus casei CH7 |
| 8 | Lactobacillus planantrum CH8 |
| 9 | Lactobacillus sakei CH9 |
| 10 | Lactobacillus curvatus CH10 |
| 11 | Lactobacillus sakei CH11 |
| 12 | Lactobacillus curvatus CH12 |
| 13 | Lactobacillus plantarum CH13 |
| 14 | Lactobacillus fermentum CH14 |
| 15 | Lactobacillus fermentum CH15 |
| 16 | Lactobacillus gasseri CH16 |
| 17 | Lactobacillus paracasei CH17 |
| 18 | Lactobacillus helveticus CH18 |
| 19 | Lactobacillus helveticus CH19 |
| 20 | Lactobacillus johnsonii CH20 |
| 21 | Lactobacillus johnsonii CH21 |
| 22 | Lactobacillus johnsonii CH22 |
| 23 | Lactobacillus brevis CH23 |
| 24 | Lactobacillus paracasei CH24 |
| 25 | Lactobacillus kimchi CH25 |
| 26 | Lactobacillus gasseri CH26 |
| 27 | Lactobacillus paracasei CH27 |
| 28 | Lactobacillus pentosus CH28 |
| 29 | Lactobacillus pentosus CH29 |
| 30 | Lactobacillus reuteri CH30 |
| 31 | Lactobacillus sakei CH31 |
| 32 | Lactobacillus johnsonii CJLJ103 |
| 33 | Lactobacillus sakei CH33 |
| 34 | Lactobacillus sakei CH34 |
| 35 | Lactobacillus plantarum CH35 |
| 36 | Lactobacillus sanfranciscensis CH36 |
| 37 | Bifidobacterium pseudocatenulatum CH37 |
| 38 | Bifidobacterium pseudocatenulatum CH38 |
| 39 | Bifidobacterium adolescentis CH39 |
| 40 | Bifidobacterium adolescentis CH40 |
| 41 | Bifidobacterium adolescentis CH41 |
| 42 | Bifidobacterium animalis CH42 |
| 43 | Bifidobacterium animalis CH43 |
| 44 | Bifidobacterium bifidum CH44 |
| 45 | Bifidobacterium bifidum CH45 |
| 46 | Bifidobacterium breve CH46 |
| 47 | Bifidobacterium breve CH47 |
| 48 | Bifidobacterium breve CH48 |
| 49 | Bifidobacterium catenulatum CH49 |

TABLE 1-continued

| Control No. | Strain name |
|---|---|
| 50 | *Bifidobacterium catenulatum* CH50 |
| 51 | *Bifidobacterium dentium* CH51 |
| 52 | *Bifidobacterium infantis* CH52 |
| 53 | *Bifidobacterium infantis* CH53 |
| 54 | *Bifidobacterium infantis* CH54 |
| 55 | *Bifidobacterium longum* CH55 |
| 56 | *Bifidobacterium longum* CH56 |
| 57 | *Bifidobacterium longum* CH57 |
| 58 | *Bifidobacterium longum* CH58 |
| 59 | *Bifidobacterium longum* CH59 |
| 60 | *Bifidobacterium longum* CH60 |

Among the strains shown in Table 1 above, *Lactobacillus brevis* CH23 was a gram-positive anaerobic *bacillus*, did not form spores, and could survive even under aerobic conditions. Furthermore, *Lactobacillus brevis* CH23 survived at 10 to 42° C. and was an acid-resistant strain stable at pH 2 for 2 hours. Furthermore, *Lactobacillus brevis* CH23 survived even in 2% sodium chloride solution and actively produced glucosidase. In addition, to chemically classify *Lactobacillus brevis* CH23, the 16S rDNA thereof was analyzed, and as a result, it was shown that *Lactobacillus brevis* CH23 had a nucleotide sequence of SEQ ID NO: 1. The 16S rDNA nucleotide sequence of *Lactobacillus brevis* CH23 was identified by BLAST in the Genebank (www.ncbi.nlm.nih.gov), and as a result, a *Lactobacillus brevis* strain having the same 16S rDNA nucleotide sequence as that of *Lactobacillus brevis* CH23 was not found, and *Lactobacillus brevis* CH23 showed a homology of 99% with the 16S rDNA sequence of *Lactobacillus brevis* strain FJ004.

Among the strains shown in Table 1 above, *Lactobacillus johnsonii* CH32 was a gram-positive anaerobic *bacillus*, did not form spores, and could survive under aerobic conditions. Furthermore, *Lactobacillus johnsonii* CH32 survived stably at a temperature of 10 to 45° C., and was an acid-resistant strain stable in pH 2 for 2 hours. Moreover, *Lactobacillus johnsonii* CH32 actively produced glucosidase, but did not produce β-glucuronidase. In addition, to chemically classify *Lactobacillus johnsonii* CH32, the 16S rDNA thereof was analyzed, and as a result, it was shown that *Lactobacillus johnsonii* CH32 had a nucleotide sequence of SEQ ID NO: 2. The 16S rDNA nucleotide sequence of *Lactobacillus johnsonii* CH32 was identified by BLAST in Genebank (www.ncbi.nlm.nih.gov), and as a result, a *Lactobacillus johnsonii* strain having the same 16S rDNA nucleotide sequence as that of *Lactobacillus johnsonii* CH32 was not found, and *Lactobacillus johnsonii* CH32 showed a homology of 99% with the 16S rDNA sequence of *Lactobacillus johnsonii* strain JCM 2012.

Among the strains shown in Table 1 above, *Bifidobacterium longum* CH57 was a gram-positive anaerobic *bacillus*, did not form spores, and showed very low viability under aerobic conditions. Furthermore, *Bifidobacterium longum* CH57 was thermally unstable. Furthermore, *Bifidobacterium longum* CH57 actively produced glucosidase, but did not produce β-glucuronidase. In addition, to chemically classify *Bifidobacterium longum* CH57, the 16S rDNA thereof was analyzed, and as a result, it was shown that *Bifidobacterium longum* CH57 had a nucleotide sequence of SEQ ID NO: 3. The 16S rDNA nucleotide sequence of *Bifidobacterium longum* CH57 was identified by BLAST in the Genebank (www.ncbi.nlm.nih.gov), and as a result, a *Bifidobacterium longum* strain having the same 16S rDNA nucleotide sequence as that of *Bifidobacterium longum* CH57 was not found, and *Bifidobacterium longum* CH57 showed a homology of 99% with the 16S rDNA sequence of *Bifidobacterium longum* strain CBT-6.

In addition, among the physiological characteristics of *Lactobacillus brevis* CH23, *Lactobacillus johnsonii* CJLJ103 and *Bifidobacterium longum* CH57, the carbon source utilization was analyzed using a sugar fermentation by an API kit (model: API 50 CHL; manufactured by BioMerieux's, USA). Table 2 below shows the results of analyzing the carbon source utilization of *Lactobacillus brevis* CH23; Table 3 below shows the results of analyzing the carbon source utilization of *Lactobacillus johnsonii* CJLJ103; and Table 4 below shows the results of analyzing the carbon source utilization of *Bifidobacterium longum* CH57. In Tables 2, 3 and 4, "+" indicates the case in which carbon source utilization is positive; "−" indicates the case in which carbon source utilization is negative; and "±" indicates the case in which carbon source utilization is ambiguous. As shown in Tables 2, 3 and 4 below, *Lactobacillus brevis* CH23, *Lactobacillus johnsonii* CJLJ103 and *Bifidobacterium longum* CH57 showed carbon source utilization different from that of other strains of the same species with respect to some carbon sources.

TABLE 2

| Carbon source | *L. brevis*[1] | *L. brevis* CH23 | Carbon source | *L. brevis*[1] | *L. brevis* CH23 |
|---|---|---|---|---|---|
| glycerol | − | − | salicin | + | + |
| erythritol | − | − | cellobiose | + | − |
| D-arabinose | − | − | maltose | + | + |
| L-arabinose | + | − | lactose | + | − |
| D-ribose | + | + | melibiose | − | + |
| D-xylose | + | + | sucrose | + | − |
| L-xylose | − | − | trehalose | + | − |
| D-adonitol | − | − | inulin | + | − |
| methyl-β-D-xylopyranoside | − | − | melezitose | + | − |
| D-galactose | + | − | raffinose | − | − |
| D-glucose | + | + | starch | − | − |
| D-fructose | + | + | glycogen | − | − |
| D-mannose | + | − | xylitol | − | − |
| L-sorbose | − | − | gentiobiose | + | − |

TABLE 2-continued

|  | Strain name | | | Strain name | |
|---|---|---|---|---|---|
| Carbon source | L. brevis[1] | L. brevis CH23 | Carbon source | L. brevis[1] | L. brevis CH23 |
| L-rhamnose | − | − | D-turanose | + | − |
| dulcitol | + | − | D-lyxose | − | − |
| inositol | − | − | D-tagatose | + | − |
| mannitol | + | − | D-fucose | − | − |
| sorbitol | + | − | L-fucose | − | − |
| α-methyl-D-mannoside | − | − | D-arabitol | − | − |
| α-methly-D-glucoside | − | − | L-arabitol | − | − |
| N-acetyl-glucosamine | + | ± | gluconate | + | ± |
| amygdalin | + | − | 2-keto-gluconate | − | − |
| arbutin | + | − | 5-keto-gluconate | − | + |
| esculin | + | + |  |  |  |

[1]Suriasih K., Aryanta WR, MahardikaG, Astawa NM. Microbiological and Chemical Properties of Kefir Made of Bali Cattle Milk. Food Science and Quality Management 2012; 6: 112-22.

TABLE 3

|  | Strain name | | | Strain name | |
|---|---|---|---|---|---|
| Carbon source | L. johnsonii[2] | L. johnsonii CJLJ103 | Carbon source | L. johnsonii[2] | L. johnsonii CJLJ103 |
| glycerol | − | − | salicin | − | − |
| erythritol | − | − | cellobiose | + | − |
| D-arabinose | − | − | maltose | − | + |
| L-arabinose | − | − | lactose | − | + |
| D-ribose | − | − | melibiose | + | − |
| D-xylose | − | − | sucrose | + | + |
| L-xylose | − | − | trehalose | + | − |
| D-adonitol | − | − | inulin | − | − |
| methyl-β-D-xylopyranoside | − | − | melezitose | − | − |
| D-galactose | − | − | raffinose | + | − |
| D-glucose | − | + | starch | − | − |
| D-fructose | − | + | glycogen | − | − |
| D-mannose | + | + | xylitol | − | − |
| L-sorbose | − | − | gentiobiose | − | + |
| L-rhamnose | − | − | D-turanose | − | − |
| dulcitol | − | − | D-lyxose | − | − |
| inositol | − | − | D-tagatose | − | − |
| mannitol | − | − | D-fucose | − | − |
| sorbitol | − | − | L-fucose | − | − |
| α-methyl-D-mannoside | − | − | D-arabitol | − | − |
| α-methly-D-glucoside | − | − | L-arabitol | − | − |
| N-acetyl-glucosamine | + | + | gluconate | − | − |
| amygdalin | − | − | 2-keto-gluconate | − | − |
| arbutin | − | − | 5-keto-gluconate | − | − |
| esculin | − | − |  |  |  |

[2]Pridmore RD, Berger B, Desiere F, Vilanova D, Barretto C, Pittet AC, Zwahlen MC, Rouvet M, Altermann E, Barrangou R, Mallet B, Mercenier A, Klaenhammer T, Arigoni F, Schell MA. The genome sequence of the probiotic intestinal bacterium Lactobacillus johnsonii NCC 533. Proc Natl Acad Sci USA. 2004 Feb. 24; 101(8): 2512-7.

TABLE 4

|  | Strain name | | | Strain name | |
|---|---|---|---|---|---|
| Carbon source | B. longum[3] | B. longum CH57 | Carbon source | B. longum[3] | B. longum CH57 |
| glycerol | ± | − | salicin | ± | − |
| erythritol | − | − | cellobiose | ± | ± |

TABLE 4-continued

| Carbon source | B. longum[3] | B. longum CH57 | Carbon source | B. longum[3] | B. longum CH57 |
|---|---|---|---|---|---|
| D-arabinose | − | − | maltose | − | − |
| L-arabinose | − | − | lactose | − | − |
| D-ribose | ± | − | melibiose | − | − |
| D-xylose | − | − | sucrose | + | ± |
| L-xylose | − | − | trehalose | ± | − |
| D-adonitol | − | − | inulin | − | − |
| methyl-β-D-xylopyranoside | − | − | melezitose | − | − |
| D-galactose | + | + | raffinose | − | − |
| D-glucose | + | + | starch | − | − |
| D-fructose | + | + | glycogen | − | − |
| D-mannose | − | − | xylitol | − | − |
| L-sorbose | − | − | gentiobiose | − | − |
| L-rhamnose | − | − | D-turanose | − | − |
| dulcitol | − | − | D-lyxose | − | − |
| inositol | − | − | D-tagatose | − | − |
| mannitol | + | − | D-fucose | − | − |
| sorbitol | − | − | L-fucose | − | − |
| α-methyl-D-mannoside | − | − | D-arabitol | − | − |
| α-methly-D-glucoside | − | − | L-arabitol | − | − |
| N-acetyl-glucosamine | ± | − | gluconate | ± | − |
| amygdalin | − | − | 2-keto-gluconate | − | − |
| arbutin | ± | − | 5-keto-gluconate | − | − |
| esculin | − | − | | | |

[3]Lukacova D, Karovucova J, Greifova M, Greif G, Sovcikova A, Kohhajdova Z. In vitro testing of selected probiotic characteristics of *Lactobacillus plantarum* and *Bifidobacterium longum*. Journal of Food and Nutrition Research 2006; 45: 77-83.

(4) Information on Deposition of Lactic Acid Bacteria

The present inventors deposited *Lactobacillus brevis* CH23 with the Korean Culture Center of Microorganisms (address: Yurim Building, 45, Hongjenae 2ga-gil, Seodaemun-gu, Seoul, Korea), an international depositary authority, on Sep. 1, 2015 under accession number KCCM 11762P. Furthermore, the present inventors deposited *Lactobacillus johnsonii* CJLJ103 with the Korean Culture Center of Microorganisms (address: Yurim Building, 45, Hongjenae 2ga-gil, Seodaemun-gu, Seoul, Korea), an international depositary authority, on Sep. 1, 2015, under accession number KCCM 11763P. Furthermore, the present inventors deposited *Bifidobacterium longum* CH57 with the Korean Culture Center of Microorganisms (address: Yurim Building, 45, Hongjenae 2ga-gil, Seodaemun-gu, Seoul, Korea)), an international depositary authority, on Sep. 1, 2015 under accession number KCCM 11764P.

2. Evaluation of the Effect of Lactic Acid Bacteria on Alleviation of Intestinal Damage or Intestinal Permeability In order to evaluate the effect of the lactic acid bacteria isolated from kimchi or human feces, on the alleviation of intestinal damage or internal permeability, the antioxidant activity, lipopolysaccharide (LPS) production inhibitory activity, β-glucuronidase (harmful intestinal enzyme) inhibitory activity, tight junction protein expression inducement activity and memory improvement activity of the lactic acid bacteria were measured.

(1) Experimental Methods

Antioxidant Activity

DPPH (2,2-diphenyl-1-picrylhydrazyl) was dissolved in ethanol to a concentration of 0.2 mM to prepare a DPPH solution. A lactic acid bacteria suspension ($1 \times 10^8$ CFU/ml) or a vitamin C solution (1 g/ml) was added to 0.1 ml of the DPPH solution and cultured at 37° C. for 20 minutes. The culture was centrifuged at 3000 rpm for 5 minutes, and the supernatant was collected. Next the absorbance of the supernatant at 517 nm was measured, and the antioxidant activity of the lactic acid bacteria was calculated.

Lipopolysaccharide (LPS) Production Inhibitory Activity

Pathogenic bacteria, such as *Escherichia coli, Klebsiella pneumonia* and *Proteus mirabilis* were separated from the elderly subject and cultured. Next, the pathogenic bacteria ($1 \times 10^5$ CFU respectively) and lactic acid bacteria ($1 \times 10^5$ CFU) were transplanted into 10 ml of sterile general anaerobic medium (GAM broth; Nissui Pharmaceutical, Japan) and anaerobically cultured for 24 hours.

Next, the culture was sonicated for about 1 hour to disrupt the outer cell membrane of the bacteria, and centrifuged at 5000×g, and the supernatant was collected. Next, the content of LPS (lipopolysaccharide) (which is a typical endotoxin) in the supernatant was measured by a LAL (Limulus Amoebocyte Lysate) assay kit (manufactured by Cape Cod Inc., USA). In addition, in order to evaluate the *E. coli* proliferation inhibitory activity of the lactic acid bacteria, the culture obtained through the same experiment as described above was diluted 1000-fold and 100000-fold and cultured in DHL medium, and then the number of *E. coli, Klebsiella pneumonia* and *Proteus mirabilis* was counted.

β-Glucuronidase Inhibitory Activity 0.1 ml of 0.1 mM p-nitrophenyl-β-D-glucuronide solution, 0.2 ml of 50 mM phosphate buffered saline and 0.1 ml of a lactic acid bacteria suspension (prepared by suspending of a lactic acid bacteria culture in 5 ml of physiological saline) were placed in a reactor and subjected to an β-glucuronidase enzymatic reaction, and 0.5 ml of 0.1 mM NaOH solution was added to stop the reaction. Next, the reaction solution was centrifuged at 3000 rpm for 5 minutes, and the supernatant was collected. Then, the absorbance of the supernatant at 405 nm was measured.

Tight Junction Protein Expression Inducement Activity

Caco2 cells obtained from the Korean Cell Line Bank were cultured in RPMI 1640 medium for 48 hours, and then the cultured Caco2 cells were dispensed to each well of a 12-well plate at a density of $2 \times 10^6$ cells/well. Next, each well was treated with 1 μg of LPS (lipopolysaccharide) or a combination of 1 μg of LPS (lipopolysaccharide) and $1 \times 10^4$ CFU of lactic acid bacteria and incubated for 24 hours. Next, the cultured cells were collected from each well, and the expression level of tight junction protein ZO-1 in the cells was measured by an immunoblotting method.

Memory Improvement Activity

SH-SY5Y cells obtained from the Korean Cell Line Bank were cultured in DMEM medium, in which 10% of FBS and 1% of antibiotics were added, and dispensed to each well of a 12-well plate at a density of $2 \times 10^6$ cells/well. Next, along with lactic acid bacteria ($1 \times 10^4$ CFU/mℓ), LPS (lipopolysaccharide), separated from *Proteus mirabilis*, was added to each well at the concentration of 0.2 mg/mℓ and cultured, and then the level of inhibition on NF-κB (nuclear factor kappa-light-chain-enhancer of activated B cells) activity and expression level of α-synuclein were measured by the immunoblotting method. NF-κB is known as a substance that causes tissue damage by inflammation reaction and aging-related diseases like Alzheimer's disease, while α-synuclein is known as a substance that causes Parkinson's disease.

(2) Experimental Results

The antioxidant activity, lipopolysaccharide (LPS) production inhibitory activity, β-glucuronidase inhibitory activity and tight junction protein expression inducement activity of the lactic acid bacteria isolated from kimchi or human feces were measured, and the results of the measurement are shown in Tables 5, 6 and 7 below. As shown in Tables 5, 6 and 7 below, *Lactobacillus curvatus* CH5, *Lactobacillus sakei* CH11, *Lactobacillus brevis* CH23, *Lactobacillus johnsonii* CJLJ103, *Bifidobacterium pseudocatenulatum* CH38 and *Bifidobacterium longum* CH57 had excellent antioxidant activity, strongly inhibited lipopolysaccharide (LPS) production and β-glucuronidase activity, strongly induced the expression of tight junction protein, strongly inhibited the NF-κB activity, and strongly inhibited the expression of α-synuclein. These lactic acid bacteria have an excellent antioxidant effect, have an excellent effect of inhibiting the enzymatic activity of intestinal flora's harmful bacteria associated with inflammation and carcinogenesis, inhibit the production of endotoxin LPS (lipopolysaccharide) produced by intestinal flora's harmful bacteria, and induce the expression of tight junction protein. Thus, these lactic acid bacteria can improve intestinal permeability syndrome. Also, the lactic acid bacteria can alleviate Alzheimer's disease and Parkinson's disease, as the lactic acid bacteria inhibit not only the production of LPS (lipopolysaccharide), an endotoxin of intestinal microorganisms, such as *K. pneumoniae*, *E. coli* and *P. mirabilis*, associated with Alzheimer's disease or Parkinson's disease, but also the production or activity of substances inducing neurodegeneration. In particular, the lactic acid bacteria are expected to bring a synergistic effect through various functions, such as alleviation of Intestinal Permeability Syndrome and inhibition on the production of endotoxin and the activity or production of substances inducing neurodegenerative.

TABLE 5

| Cont No. | Strain name | Antioxidant activity | β-glucuronidase inhibitory activity | tight junction protein expression inducement activity | SH-SY5Y cell inhibition on NF-κB | inhibition on α-synuclein | LPS production inhibitory K. pneupomiae | E. coli | P. mirabilis |
|---|---|---|---|---|---|---|---|---|---|
| 1 | L. acidophilus CH1 | + | + | − | − | − | − | − | − |
| 2 | L. acidophilus CH2 | + | + | − | − | − | + | + | + |
| 3 | L. acidophilus CH3 | + | + | − | − | − | + | + | + |
| 4 | L. brevis CH4 | + | + | − | ++ | + | − | + | + |
| 5 | L. curvatus CH5 | +++ | + | ++ | ++ | + | + | + | + |
| 6 | L. brevis CH6 | + | + | − | + | − | − | − | − |
| 7 | L. casei CH7 | + | + | − | − | − | − | − | − |
| 8 | L. planantrum CH8 | + | + | − | + | − | + | + | + |
| 9 | L. sakei CH9 | − | + | − | − | − | − | − | − |
| 10 | L. curvatus CH10 | − | + | − | + | − | − | − | − |
| 11 | L. sakei CH11 | +++ | + | ++ | ++ | ++ | ++ | + | + |
| 12 | L. curvatus CH12 | − | + | + | + | + | − | − | − |
| 13 | L. plantarum CH13 | − | + | − | + | − | − | − | − |

TABLE 5-continued

| Cont No. | Strain name | Antioxidant activity | β-glucuronidase inhibitory activity | tight junction protein expression inducement activity | SH-SY5Y cell inhibition on NF-κB | SH-SY5Y cell inhibition on α-synuclein | LPS production inhibitory K. pneupomiae | LPS production inhibitory E. coli | LPS production inhibitory P. mirabilis |
|---|---|---|---|---|---|---|---|---|---|
| 14 | L. fermentum CH14 | − | + | − | − | + | − | − | − |
| 15 | L. fermentum CH15 | +++ | + | − | − | − | + | + | + |
| 16 | L. gasseri CH16 | + | + | − | − | − | + | + | + |
| 17 | L. paracasei CH17 | + | + | − | + | − | − | − | − |
| 18 | L. helveticus CH18 | + | + | − | − | − | − | − | − |
| 19 | L. helveticus CH19 | + | + | − | − | − | − | − | − |
| 20 | L. johnsonii CH20 | + | + | + | + | + | − | − | − |

TABLE 6

| Cont No. | Strain name | Antioxidant activity | β-glucuronidase inhibitory activity | tight junction protein expression inducement activity | SH-SY5Y cell inhibition on NF-κB | SH-SY5Y cell inhibition on α-synuclein | LPS production inhibitory K. pneupomiae | LPS production inhibitory E. coli | LPS production inhibitory P. mirabilis |
|---|---|---|---|---|---|---|---|---|---|
| 21 | L. johnsonii CH21 | + | + | + | + | ++ | + | + | + |
| 22 | L. johnsonii CH22 | + | + | + | + | + | − | − | − |
| 23 | L. brevis CH23 | +++ | + | ++ | ++ | + | ++ | ++ | ++ |
| 24 | L. paracasei CH24 | + | + | − | − | − | − | − | − |
| 25 | L. kimchi CH25 | + | + | − | − | − | − | − | − |
| 26 | L. gasseri CH26 | + | + | − | − | − | − | − | − |
| 27 | L. paracasei CH27 | + | + | + | + | − | − | − | − |
| 28 | L. pentosus CH28 | + | + | − | + | + | − | − | − |
| 29 | L. pentosus CH29 | + | + | − | − | − | − | − | − |
| 30 | L. reuteri CH30 | + | − | − | − | − | − | − | − |
| 31 | L. sakei CH31 | − | + | + | + | + | − | − | − |
| 32 | L. johnsonii CJLJ103 | +++ | + | ++ | ++ | +++ | ++ | ++ | +++ |
| 33 | L. sakei CH33 | + | + | + | − | + | − | − | − |
| 34 | L. sakei CH34 | + | + | + | − | + | + | + | + |
| 35 | L. plantarum CH35 | + | + | + | + | + | + | + | + |
| 36 | L. sanfranciscensis CH36 | + | + | + | + | + | + | − | − |
| 37 | B. pseudocatenulatum CH37 | − | + | + | + | + | − | − | − |
| 38 | B. pseudocatenulatum CH38 | +++ | + | ++ | + | ++ | + | + | + |
| 39 | B. adolescentis CH39 | − | + | + | + | + | − | − | − |
| 40 | B. adolescentis CH40 | − | + | + | + | + | + | + | + |

TABLE 7

| Cont No. | Strain name | Antioxidant | β-glucuronidase inhibitory | tight junction protein expression inducement | SH-SY5Y cell inhibition on NF-κB | SH-SY5Y cell inhibition on α-synuclein | LPS production inhibitory K. pneupomiae | LPS production inhibitory E. coli | LPS production inhibitory P. mirabilis |
|---|---|---|---|---|---|---|---|---|---|
| 41 | B. adolescentis CH41 | + | + | + | + | + | + | + | + |
| 42 | B. animalis CH42 | + | + | − | + | − | − | − | − |
| 43 | B. animalis CH43 | + | + | − | + | − | − | − | − |
| 44 | B. bifidum CH44 | + | + | − | + | − | − | − | − |
| 45 | B. bifidum CH45 | + | + | − | + | − | − | − | − |
| 46 | B. breve CH46 | + | − | − | − | − | − | + | + |
| 47 | B. breve CH47 | + | + | + | ++ | + | − | − | − |
| 48 | B. breve CH48 | + | + | + | + | + | − | − | − |
| 49 | B. catenulatum CH49 | + | + | ++ | + | ++ | − | − | − |
| 50 | B. catenulatum CH50 | − | + | − | + | − | − | − | − |
| 51 | B. dentium CH51 | + | − | − | − | − | − | − | − |
| 52 | B. infantis CH52 | − | + | − | − | − | − | − | − |
| 53 | B. infantis CH53 | − | + | − | + | − | − | − | − |
| 54 | B. infantis CH54 | + | + | − | − | − | − | − | − |
| 55 | B. longum CH55 | + | + | + | + | + | − | − | − |
| 56 | B. longum CH56 | +++ | + | + | + | + | ++ | − | − |
| 57 | B. longum CH57 | +++ | + | ++ | + | ++ | +++ | + | ++ |
| 58 | B. longum CH58 | + | + | + | + | + | + | + | + |
| 59 | B. longum CH59 | + | + | + | + | + | + | + | + |
| 60 | B. longum CH60 | + | − | + | − | + | − | − | − |

The final concentration of lactic acid bacteria in measurement of antioxidant activity: 1 × 10⁴ CFU/ml;
the concentration of lactic acid bacteria added for measurement of beta-glucuronidase inhibitory activity and lipopolysaccharide (LPS) production inhibitory activity: 1 × 10⁴ CFU/ml;
the concentration of lactic acid bacteria in measurement of tight junction protein expression inducement activity: 1 × 10⁴ CFU/ml.
Criteria for measurement of various activities of lactic acid bacteria: very strongly (+++; >90%); strongly (++; >60-90%); weakly (+;>20-60%); not or less than 20% (−; <20%).

3. Measurement of Improvement Effect of Lactic Acid Bacteria for Cognitive Ability by Using Model Animals with Induced Memory Damage (1) Selection of Lactic Acid Bacteria for Experiment to Measure Improvement Effect for Cognitive Ability The following 13 types of lactic acid bacteria were selected as lactic acid bacteria for the experiment to measure improvement effect for cognitive ability among a total of 60 types of lactic acid bacteria isolated from Kimchi or human feces.

*Lactobacillus acidophilus* CH3, *Lactobacillus curvatus* CH5, *Lactobacillus sakei* CH11, *Lactobacillus fermentum* CH15, *Lactobacillus johnsonii* CH21, *Lactobacillus brevis* CH23, *Lactobacillus johnsonii* CJLJ103, *Lactobacillus plantarum* CH35, *Bifidobacterium pseudocatenulatum* CH38, *Bifidobacterium adolescentis* CH41, *Bifidobacterium longum* CH56, *Bifidobacterium longum* CH57, *Bifidobacterium longum* CH59

(2) Passive Avoidance Test and the Result

In the Passive Avoidance test apparatus, which is divided into the first and second space, there is a guillotine-like door that connects the two spaces. By using lightings, the first space was kept bright while the second space was kept dark. On the floor of the second space that was kept dark was placed an electric grid that flowed 0.5 mA of electric shock for three seconds in the case of the animal moving to the dark space.

The selected 13 types of lactic acid bacteria were each suspended in physiological saline at the concentration of 1×10¹⁰ CFU/mℓ, and then the suspension was administered to mice of the test animal (5-week-old ICR male mice from Raonbio), at the dosage of 0.1 mℓ (equivalent to 1×10⁹ CFU of lactic acid bacteria) on a daily basis for three days. Also, 0.1 mℓ of physiological saline were administered to the mice corresponding to the normal group and memory impairment group on a daily basis for three days. The mice corresponding to the positive control group were administered with 5 mg/kg (body weight) of the positive control drug, donepezil (treatment for Alzheimer's disease and Alzheimer's disease-type dementia), on a daily basis for three days. The number of mice per the experimental group was 9.

On the second day after administering the drug, the above mice were placed in the first space which was bright, observed for 20 seconds, and allowed to move into the second space that was kept dark by opening the guillotine-like door. The mice, which did not move to the second space for 60 seconds after the door was opened, were excluded from the experiment. Once the mice move to the second space, the guillotine-like door is closed, and the mice receive the electric shock at 0.5 mA through the grid on the floor for three seconds. The mice are forced to remember the shock. On the third day after administering the drug, an hour after administering lactic acid bacteria or positive control drug, 1 mg/kg (body weight) of scopolamine (cholinergic blocking drug inducing cognitive ability disorder or memory damage), dissolved in distilled water, was administered in the abdomen while the normal group was administered with physiological saline in the abdomen. The experiment was conducted by using Passive Avoidance experiment apparatus after 30 minutes of administration of scopolamine. With 10 seconds of observation, the guillotine-like door is opened, the time that the mice in each experimental group took to have all of their four feet inside the second space was measured up to 300 seconds, whose result is shown in Table 8. The result in Table 8 shows that longer latency time means better performance in learning passive avoidance and recovering short-term memory.

TABLE 8

| Group | Latency time; sec |
| --- | --- |
| Normal group | 240.2 |
| Memory damage group only administered scopolamine | 22.6 |
| Positive group administered scopolamine and donepezil | 66.4 |
| Administered scopolamine and Lactobacillus acidophilus CH3 | 33.5 |
| Administered scopolamine and Lactobacillus curvatus CH5 | 57.4 |
| Administered scopolamine and Lactobacillus sakei CH11 | 45.0 |
| Administered scopolamine and Lactobacillus fermentum CH15 | 56.7 |
| Administered scopolamine and Lactobacillus johnsonii CH21 | 22.4 |
| Administered scopolamine and Lactobacillus brevis CH23 | 61.2 |
| Administered scopolamine and Lactobacillus johnsonii CJLJ103 | 71.0 |
| Administered scopolamine and Lactobacillus plantarum CH35 | 44.6 |
| Administered scopolamine and Bifidobacterium pseudocatenulatum CH38 | 49.6 |
| Administered scopolamine and Bifidobacterium adolescentis CH41 | 35.6 |
| Administered scopolamine and Bifidobacterium longum CH56 | 54.9 |
| Administered scopolamine and Bifidobacterium longum CH57 | 62.1 |
| Administered scopolamine and Bifidobacterium longum CH59 | 48.5 |

As shown in Table 8, when model animals, induced to have cognitive ability disorder or memory impairment by scopolamine, were administered with *Lactobacillus brevis* CH23, *Lactobacillus johnsonii* CJLJ103 or *Bifidobacterium longum* CH57, latency time significantly increased compared to the memory impairment group administered with only scopolamine, and especially, administration of *Lactobacillus johnsonii* CJLJ103 showed better effect than the administration of donepezil, a commercial treatment.

(3) Y-Maze Test and the Result

Apparatus used in the Y-maze test consists of three arms with each being 42 cm in length, 3 cm in width and 12 cm in height. The three arms, made from black polyvinyl resin, were placed at an angle of 120 degrees.

The selected 13 types of lactic acid bacteria were each suspended in physiological saline at the concentration of $1 \times 10^{10}$ CFU/mℓ, and then the suspension was administered to mice of the test animal (5-week-old ICR male mice from Raonbio), at the dosage of 0.1 mℓ (equivalent to $1 \times 10^9$ CFU of lactic acid bacteria) on a daily basis for three days. Also, 0.1 mℓ of physiological saline were administered to the mice corresponding to the normal group and memory impairment group on a daily basis for three days. The mice corresponding to the positive control group were administered with 5 mg/kg (body weight) of the positive control drug, donepezil (treatment for Alzheimer's disease and Alzheimer's disease-type dementia), on a daily basis for three days. The number of mice per experimental group was 9.

An hour after the final administration of lactic acid bacteria or positive control drug, 1 mg/kg (body weight) of scopolamine (cholinergic blocking drug inducing cognitive ability disorder or memory impairment), dissolved in distilled water, was administered in the abdomen while the normal group was administered with physiological saline in the abdomen. half an hour after the administration of scopolamine, the mouse was carefully placed in one of the three arms, A, B, and C, in the Y-maze and allowed to freely move for eight minutes, and then the arm in which the mouse moved was recorded. In the experiment, the arm was recorded as a case in which the test animal moved only when the entire body including the tail was inside the arm, or when the mouse moved back in. In the case of the mouse moving into each arm sequentially, one point (actual alteration) was allocated. Alteration behavior is defined as a case where the mouse moved in all of the three arms sequentially. The experimental result was calculated by the formula below (Sarter, M. et al., Psychopharmacology., 94, pp 491-495, 1998), as shown in Table 9 below.

Spontaneous alteration (%)=actual alternation/maximum alternation×100 (maximum alteration: the total number of entries−2)

Table 9 below shows that greater alternation behavior (unit: %) means better recovery of learning and spatial memory.

TABLE 9

| Group | Alternation behavior; % |
| --- | --- |
| Normal group | 74.5 |
| Memory damage group only administered scopolamine | 49.9 |
| Positive group administered scopolamine and donepezil | 65.8 |
| Administered scopolamine and Lactobacillus acidophilus CH3 | 53.7 |
| Administered scopolamine and Lactobacillus curvatus CH5 | 51.3 |
| Administered scopolamine and Lactobacillus sakei CH11 | 49.0 |
| Administered scopolamine and Lactobacillus fermentum CH15 | 56.2 |
| Administered scopolamine and Lactobacillus johnsonii CH21 | 53.5 |

TABLE 9-continued

| Group | Alternation behavior; % |
|---|---|
| Administered scopolamine and Lactobacillus brevis CH23 | 59.2 |
| Administered scopolamine and Lactobacillus johnsonii CJLJ103 | 63.9 |
| Administered scopolamine and Lactobacillus plantarum CH35 | 52.4 |
| Administered scopolamine and Bifidobacterium pseudocatenulatum CH38 | 52.5 |
| Administered scopolamine and Bifidobacterium adolescentis CH41 | 54.1 |
| Administered scopolamine and Bifidobacterium longum CH56 | 55.2 |
| Administered scopolamine and Bifidobacterium longum CH57 | 60.3 |
| Administered scopolamine and Bifidobacterium longum CH59 | 55.5 |

As shown in Table 9, when model animals, induced to have cognitive ability disorder or memory impairment by scopolamine, were administered with Lactobacillus brevis CH23, Lactobacillus johnsonii CJLJ103 or Bifidobacterium longum CH57, alternation behavior significantly increased compared to the memory impairment group administered with only scopolamine, and especially, administration of Lactobacillus johnsonii CJLJ103 showed excellent effect equivalent to the administration of donepezil, a commercial treatment.

4. Preparation of Red Bean Ferment by Using Lactic Acid Bacteria and Measurement of Improvement Effect of the Red Bean Ferment for Cognitive Ability (1) Preparation of Red Bean Ferment Lactobacillus johnsonii CJLJ103 was cultured in the edible TS medium and centrifuged at 10,000gf for 20 minutes to yield Lactobacillus johnsonii CJLJ103 biomass. The yielded Lactobacillus johnsonii CJLJ103 biomass was washed with physiological saline twice and suspended in 100 ml of physiological saline to prepare the suspension of Lactobacillus johnsonii CJLJ103 biomass. Next, 10 g of finely crushed red bean was added to 90 ml of suspension of Lactobacillus johnsonii CJLJ103 biomass, which was then cultured for 24 hours to ferment red bean. Next, the red bean ferment liquid was freeze-dried to yield red bean ferment.

(2) Passive Avoidance Test and the Result

Except the type and amount of administered drug, Passive Avoidance test was conducted in the same way as stated earlier herein, and the result is shown in Table 10 below. As shown in Table 10, administration of the red bean suspension or Lactobacillus johnsonii CJLJ103 (daily dosage: 2×10$^8$ CFU/mouse) failed to significantly improve the damaged memory while the administration of the red bean ferment significantly improved the damaged memory.

TABLE 10

| Group | Alternation behavior; % |
|---|---|
| Normal group | 232.5 |
| Memory damage group only administered scopolamine | 23.8 |
| Positive group administered scopolamine and donepezil | 65.7 |
| Administered scopolamine and red bean suspension | 48.5 |
| Administered scopolamine and Lactobacillus johnsonii CJLJ103 | 48.0 |

TABLE 10-continued

| Group | Alternation behavior; % |
|---|---|
| Administered scopolamine and red bean ferment | 64.2 |

1) Red bean suspension was prepared by suspending red bean powder in physiological saline, and the daily dosage was 0.2 g per mouse based on the amount of red bean powder.
2) Lactobacillus johnsonii CJLJ103 was administered after suspended in physiological saline, and the daily dosage was 2 × 10$^8$ CFU per mouse based on the amount of Lactobacillus johnsonii CJLJ103.
3) Red bean ferment was administered after suspended in physiological saline, and the daily dosage was 0.2 g per mouse based on the amount of red bean ferment. The 0.2 g of red bean ferment contained approximately 2 × 10$^8$ CFU of Lactobacillus johnsonii CJLJ103.

(3) Y-Maze Test and the Result

Except the type and amount of administered drug, Y-maze test was conducted in the same way as stated earlier herein, and the result is shown in Table 11 below. As shown in Table 11, administration of the red bean suspension or Lactobacillus johnsonii CJLJ103 (daily dosage: 2×10$^8$ CFU/mouse) to the mouse failed to significantly improve the damaged memory while the administration of the red bean ferment significantly improved the damaged memory.

TABLE 11

| Group | Alternation behavior; % |
|---|---|
| Normal group | 75.2 |
| Memory damage group only administered scopolamine | 45.4 |
| Positive group administered scopolamine and donepezil | 63.2 |
| Administered scopolamine and red bean suspension | 52.4 |
| Administered scopolamine and Lactobacillus johnsonii CJLJ103 | 57.6 |
| Administered scopolamine and red bean ferment | 63.3 |

1) Red bean suspension was prepared by suspending red bean powder in physiological saline, and the daily dosage was 0.2 g per mouse based on the amount of red bean powder.
2) Lactobacillus johnsonii CJLJ103 was administered after suspended in physiological saline, and the daily dosage was 2 × 10$^8$ CFU per mouse based on the amount of Lactobacillus johnsonii CJLJ103.
3) Red bean ferment was administered after suspended in physiological saline, and the daily dosage was 0.2 g per mouse based on the amount of red bean ferment. The 0.2 g of red bean ferment contained approximately 2 × 10$^8$ CFU of Lactobacillus johnsonii CJLJ103.

5. Measurement of Improvement Effect of Lactic Acid Bacteria for Cognitive Ability by Using Model Animals Induced to have Memory Impairment by Escherichia coli (1) Inducement of Memory Impairment and Administration of Drug Escherichia coli K20 separated from the animal with impaired memory was administered to the mouse to induce memory impairment, and the improvement effect of lactic acid bacteria for cognitive ability was measured by conducting Y-maze test and Passive Avoidance test.

In more detail, Escherichia coli K20 was administered to a mouse (5-week-old ICR male mice from Raonbio) that was fed for a week in the animal laboratory at the dosage of 1×10$^9$ CFU on a daily basis for five days to induce memory impairment. In the meantime, the normal group was administered with physiological saline instead of Escherichia coli K20. From the next day of the final administration of Escherichia coli K20, lactic acid bacteria suspension (lactic acid bacteria suspended in physiological saline at the concentration of 1×10$^{10}$ CFU/ml) was administered to the mouse induced to have memory impairment at the dosage of 0.1 ml (equivalent to 1×10$^9$ CFU of lactic acid bacteria) on a daily basis for five days. Also, the normal group and memory impairment-induced group were administered with 0.1 ㎖ of physiological saline on a daily basis for five days. In addition, lactic acid bacteria suspension (lactic acid bacteria suspended in physiological saline at the concentration of $1\times10^{10}$ CFU/㎖) was administered to the normal group at the dosage of 0.1 ㎖ (equivalent to $1\times10^9$ CFU of lactic acid bacteria) on a daily basis for five days, which was used as a positive control group. The number of mice per experimental group was 9.

(2) Y-Maze Test

An hour after the final administration of drug, the mouse was carefully placed in one of the three arms, A, B, and C, in the Y-maze and allowed to freely move for eight minutes, and then the arm in which the mouse moved was recorded. In the experiment, the arm was recorded as a case in which the test animal moved only when the entire body including the tail was inside the arm, or when the mouse moved back in. In the case of the mouse moving into each arm sequentially, one point (actual alteration) was allocated. Alteration behavior is defined as a case where the mouse moved in all of the three arms sequentially. The experimental result was calculated by the formula below (Sarter, M. et al., Psychopharmacology., 94, pp 491-495, 1998).

Spontaneous alteration (%)=actual alternation/maximum alternation×100 (maximum alteration: the total number of entries−2)

(3) Passive Avoidance Test

On the second day after administering the drug, the above mice were placed in the first space which was bright, observed for 20 seconds, and allowed to move into the second space that was kept dark by opening the guillotine-like door. The mice, which did not move to the second space for 60 seconds after the door was opened, were excluded from the experiment. Once the mice move to the second space, the guillotine-like door is closed, and the mice receive the electric shock at 0.5 mA through the grid on the floor for three seconds. The mice are forced to remember the shock.

An hour after the final administration of drug, the experiment was conducted by using the Passive Avoidance test apparatus. With 10 seconds of observation, the guillotine-like door is opened, the time that the mice in each experimental group took to have all of their four feet inside the second space was measured up to 300 seconds.

(3) Measurement of the Expression Level of Nerve Growth-Promoting Factor

Two hours after the final administration of drug, hippocampus was separated from the mice of each experimental group, and the expression level of BDNF (Brain-Derived Neurotrophic Factor), known as a nerve growth-promoting factor, and the activity level of CREB (Cydic AMP Response Element-Binding), known as a memory-improving transcription factor, were measured.

(4) Experimental Result

Figure 2:
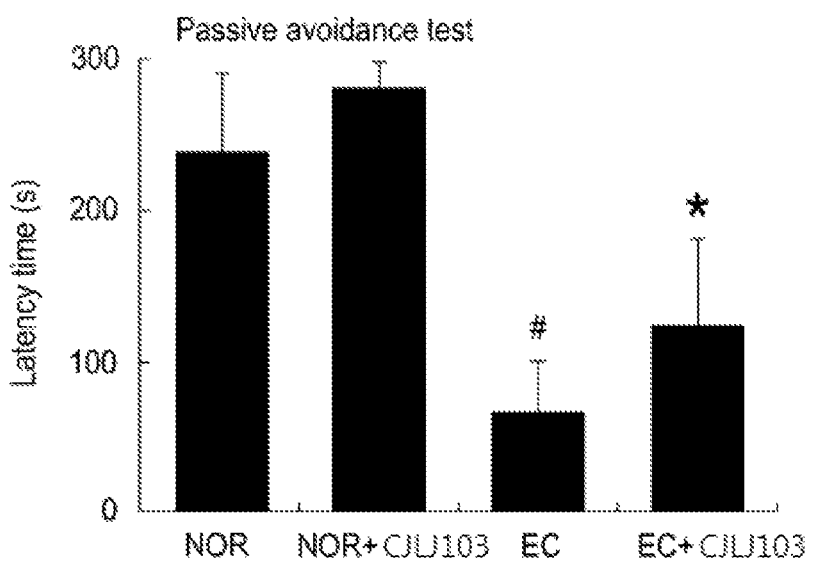
FIG. 2 is a graph showing the impact that administration of *Lactobacillus johnsonii* CJLJ103 has on the Passive Avoidance test of model animals induced to have memory impairment by *Escherichia coli* K20.
Figure 3:
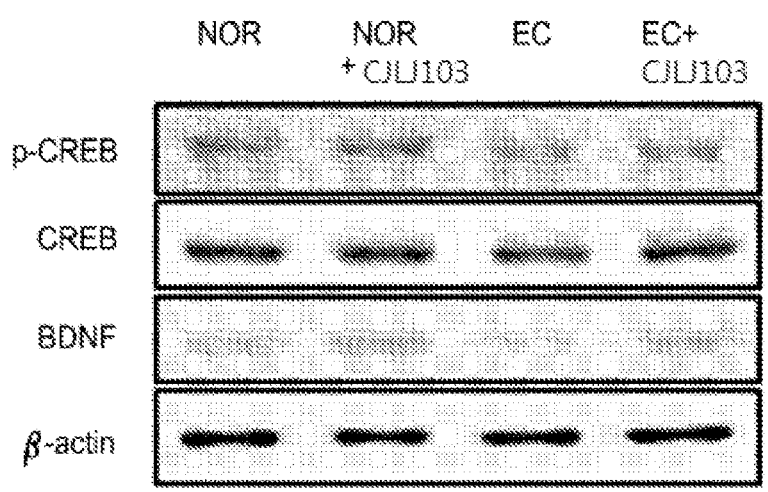
FIG. 3 is a photo showing the impact that administration of *Lactobacillus johnsonii* CJLJ103 has on the expression level of nerve growth-promoting factor of model animals induced to have memory impairment by *Escherichia coli* K20.

FIG. 1 is a graph showing the impact that administration of *Lactobacillus johnsonii* CJLJ103 has on the Y-maze test of model animals induced to have memory impairment by *Escherichia coli* K20. FIG. 2 is a graph showing the impact that administration of *Lactobacillus johnsonii* CJLJ103 has on the Passive Avoidance test of model animals induced to have memory impairment by *Escherichia coli* K20 flora. FIG. 3 is a photo showing the impact that administration of *Lactobacillus johnsonii* CJLJ103 has on the expression level of nerve growth-promoting factor of model animals induced to have memory impairment by *Escherichia coli* K20.

From FIG. 1 to FIG. 3, "NOR" means the normal group, "NOR+CJLJ103" means the experimental group administered *Lactobacillus johnsonii* CJLJ103 in the normal group, "EC" is the memory impairment-induced group where only *Escherichia coli* K20 was administered, and "EC+CJLJ103" means the experimental group where memory impairment was induced by administering *Escherichia coli* K20 and then *Lactobacillus johnsonii* CJLJ103 was administered. As shown from FIG. 1 to FIG. 3, administration of *Lactobacillus johnsonii* CJLJ103 to the normal group did not show significance while showing a slight existence of memory. On the other hand, administration of *Lactobacillus johnsonii* CJLJ103 to the mice induced to have memory impairment by *Escherichia coli* K20 significantly improved memory while improving the expression level of BDNF in hippocampus as well as the amount of activity (phosphorylation) of CREB.

6. Measurement of Improvement Effect of Lactic Acid Bacteria for Cognitive Ability by Using Model Animals with Induced Memory Impairment by Proteusmirabilis

*Proteus mirabilis* K21 separated from the animal with damaged memory was administered to the mice to induce memory impairment (similar symptoms to Parkinson's disease), and Y-maze test was conducted to measure the improvement effect of lactic acid bacteria for cognitive ability.

In more detail, *Proteus mirabilis* K21 was administered to a mouse (5-week-old ICR male mice from Raonbio) that was fed for a week in the animal laboratory at the dosage of $1\times10^9$ CFU on a daily basis for five days to induce memory impairment. In the meantime, the normal group was administered with physiological saline instead of *Proteus mirabilis* K21. From the next day of the final administration of *Proteus mirabilis* K21, lactic acid bacteria suspension (lactic acid bacteria suspended in physiological saline at the concentration of $1\times10^{10}$ CFU/㎖) was administered to the mouse induced to have memory impairment at the dosage of 0.1 ㎖ (equivalent to $1\times10^9$ CFU of lactic acid bacteria) on a daily basis for five days. Also, the normal group and memory impairment-induced group were administered with 0.1 ㎖ of physiological saline on a daily basis for five days. In addition, donepezil (treatment for Alzheimer's disease and Alzheimer's disease-type dementia), a positive control drug, was administered to the positive control group at the dosage of 5 mg/kg (body weight) on a daily basis for five days. The number of mice per experimental group was 9.

An hour after the final administration of drug, the mouse was carefully placed in one of the three arms, A, B, and C, in the Y-maze and allowed to freely move for eight minutes, and then the arm in which the mouse moved was recorded. In the experiment, the arm was recorded as an arm in which the test animal moved only when the entire body including the tail was inside the arm, or when the mouse moved back in. In the case of the mouse moving into each arm sequentially, one point (actual alteration) was allocated. Alteration behavior is defined as a case where the mouse moved in all of the three arms sequentially. The experimental result was calculated by the formula below (Sarter, M. et al., Psychopharmacology., 94, pp 491-495, 1998), as shown in Table 12 below.

Spontaneous alteration (%)=actual alternation/maximum alternation×100 (maximum alteration: the total number of entries−2)

Table 12 below shows that greater alternation behavior (unit: %) means better recovery of learning and spatial memory.

TABLE 12

| Group | Alternation behavior; % |
|---|---|
| Normal group | 73.8 |
| Memory damage group only administered Proteus mirabilis K21 | 46.4 |
| Positive group administered Proteus mirabilis K21 and donepezil | 58.6 |
| Administered Proteus mirabilis K21 and Lactobacillus acidophilus CH3 | 52.5 |
| Administered Proteus mirabilis K21 and Lactobacillus curvatus CH5 | 50.2 |
| Administered Proteus mirabilis K21 and Lactobacillus sakei CH11 | 50.7 |
| Administered Proteus mirabilis K21 and Lactobacillus fermentum CH15 | 55.5 |
| Administered Proteus mirabilis K21 and Lactobacillus johnsonii CH21 | 54.7 |
| Administered Proteus mirabilis K21 and Lactobacillus brevis CH23 | 53.3 |
| Administered Proteus mirabilis K21 and Lactobacillus johnsonii CJLJ103 | 62.8 |
| Administered Proteus mirabilis K21 and Lactobacillus plantarum CH35 | 54.1 |
| Administered Proteus mirabilis K21 and Bifidobacterium pseudocatenulatum CH38 | 51.2 |
| Administered Proteus mirabilis K21 and Bifidobacterium adolescentis CH41 | 55.3 |
| Administered Proteus mirabilis K21 and Bifidobacterium longum CH56 | 54.8 |
| Administered Proteus mirabilis K21 and Bifidobacterium longum CH57 | 57.3 |
| Administered Proteus mirabilis K21 and Bifidobacterium longum CH59 | 54.9 |

As shown in Table 12, administration of *Lactobacillus johnsonii* CJLJ103 to model animals induced to have memory impairment by *Proteus mirabilis* K21 flora showed better effect than the administration of donepezil, a commercial treatment.

Although the present invention has been described above with reference to the examples, the scope of the present invention is not limited to these examples, and various modifications are possible without departing from the scope and idea of the present invention. Therefore, the scope of protection of the present invention should be interpreted to include all embodiments falling within the appended claims.

The invention claimed is:

1. A freeze-dried food composition, comprising:
   *Lactobacillus johnsonii* CJLJ103 (accession number: KCCM 11763P), a culture thereof, a lysate thereof on an extract thereof; and
   a natural carbohydrate.

2. The food composition according to claim 1, wherein the natural carbohydrate is a member of the group consisting of monosaccharides, disaccharides, polysaccharides and mixtures thereof.

3. The food composition according to claim 1, wherein the food composition is for improving or alleviating or treating memory loss in a subject suffering from a degenerative disease or cognitive function disorder, and the degenerative brain disease is selected from the group consisting of Alzheimer's disease, Parkinson's disease, Huntington's disease and dementia.

4. The food composition according to claim 3, wherein the dementia is selected from the group consisting of senile dementia, vascular dementia, Lewy body dementia, frontotemporal dementia, Alzheimer's disease-type dementia, Parkinson's disease-type dementia, Huntington's disease-type dementia, Creutzfeldt-Jacob disease-type dementia and Pick's disease-type dementia, normal pressure hydrocephalus-causing dementia and head injury-causing dementia.

5. The food composition according to claim 1, wherein the food composition is for improving memory or learning ability.

6. The food composition according to claim 1, wherein the food composition is probiotic and the CJLJ103 strain is alive.

7. The food composition according to claim 1, further comprising a red bean ferment by *Lactobacillus johnsonii* CJLJ103.

8. The food composition according to claim 2, wherein the natural carbohydrate is selected from the group consisting of glucose, fructose, maltose, sucrose, dextrin, cyclodextrin, xylitol, sorbitol, erythritol and mixtures thereof.

* * * * *

SEQUENCE LISTING

<160> NUMBER OF SEQ ID NOS: 3

<210> SEQ ID NO 1
<211> LENGTH: 1132
<212> TYPE: DNA
<213> ORGANISM: Lactobacillus brevis

<400> SEQUENCE: 1

```
agggataaca cttggaaaca ggtgctaata ccgtataaca acaaaatccg catggatttt      60
gtttgaaagg tggcttcggc tatcacttct ggatgatccc gcggcgtatt agttagttgg     120
tgaggtaaag gcccaccaag acgatgatac gtagccgacc tgagagggta atcggccaca     180
ttgggactga gacacggccc aaactcctac gggaggcagc agtagggaat cttccacaat     240
ggacgaaagt ctgatggagc aatgccgcgt gagtgaagaa gggtttcggc tcgtaaaact     300
ctgttgttaa agaagaacac ctttgagagt aactgttcaa gggttgacgg tatttaacca     360
gaaagccacg gctaactacg tgccagcagc cgcggtaata cgtaggtggc aagcgttgtc     420
cggatttatt gggcgtaaag cgagcgcagg cggttttta agtctgatgt gaaagccttc     480
ggcttaaccg gagaagtgca tcggaaactg ggagacttga gtgcagaaga ggacagtgga     540
actccatgtg tagcggtgga atgcgtagat atatggaaga acaccagtgg cgaaggcggc     600
tgtctagtct gtaactgacg ctgaggctcg aaagcatggg tagcgaacag gattagatac     660
cctgstagtc catgccgtaa acgatgagtg ctaagtgttg gagggtttcc gcccttcagt     720
gctgcagcta acgcattaag cactccgcct ggggagtacg accgcaaggt tgaaactcaa     780
aggaattgac gggggcccgc acaagcggtg gagcatgtgg tttaattcga agctacgcga     840
agaaccttac caggtcttga catcttctgc caatcttaga gataagacgt tcccttcggg     900
gacagaatga caggtggtgc atggttgtcg tcagctcgtg tcgtgagatg ttgggttaag     960
tcccgcaacg agcgcaaccc ttattatcag ttgccagcat tcagttgggc actctggtga    1020
gactgccggt gacaaaccgg aggaaggtgg ggatgacgtc aaatcatcat gccccttatg    1080
acctgggcta cacacgtgct acaatggacg gtacaacgag tcgcgaagtc gt            1132
```

<210> SEQ ID NO 2
<211> LENGTH: 1258
<212> TYPE: DNA
<213> ORGANISM: Lactobacillus johnsonii

<400> SEQUENCE: 2

```
gtaacttgcc caagagactg ggataacacc tggaaacaga tgctaatacc ggataacaac      60
actagacgca tgtctagagt ttgaaagatg gttctgctat cactcttgga tggacctgcg     120
gtgcattagc tagttggtaa ggtaacggct taccaaggca atgatgcata gccgagttga     180
gagactgatc ggccacattg ggactgagac acggcccaaa ctcctacggg aggcagcagt     240
agggaatctt ccacaatgga cgaaagtctg atggagcaac gccgcgtgag tgaagaaggg     300
tttcggctcg taaagctctg ttggtagtga agaaagatag aggtagtaac tggccttgat     360
ttgacggtaa ttccccagaa agtcacggct aactacgtgc cagcagccgc ggtaatacgt     420
aggtggcaag cgttgtccgg atttattggg cgtaaagcga gtgcaggcgg ttcaataagt     480
ctgatgtgaa agccttcggc tcaaccggag aattgcatca gaaactgttg aacttgagtg     540
cagaagagga gagtggaact ccatgtgtag cggtggaatg cgtagatata tggaagaaca     600
ccagtggcga aggcggctct ctggtctgca actgacgctg aggctcgaaa gcatgggtag     660
cgaacaggat tagataccct ggtagtccat gccgtaaacg atgagtgcta agtgttggga     720
ggtttccgcc tctcagtgct gcagctaacg cattaagcac tccgcctggg gagtacgacc     780
gcaaggttga aactcaaagg aattgacggg ggcccgcaca gcggtggag catgtggttt      840
aattcgaagc aacgcgaaga accttaccag gtcttgacat ccagtgcaaa cctaagagat     900
taggtgttcc cttcggggac gctgagacag gtggtgcatg gctgtcgtca gctcgtgtcg     960
tgagatgttg ggttaagtcc cgcaacgagc gcaacccttg tcattagttg ccatcattaa    1020
gttgggcact ctaatgagac tgccggtgac aaaccggagg aaggtgggga tgacgtcaag    1080
tcatcatgcc ccttatgacc tgggctacac acgtgctaca atggacggta caacgagaag    1140
cgaacctgcg aaggcaagcg atctcttaa agccgttctc agttcggact gtaggctgca    1200
actcgcctac acgaagctgg aatcgctagt aatcgcggaa cagtacgccg cggtgaat    1258
```

<210> SEQ ID NO 3
<211> LENGTH: 1348
<212> TYPE: DNA
<213> ORGANISM: Bifidobacterium longum

<400> SEQUENCE: 3

```
cgggctttgc ttggtggtga gagtggcgaa cgggtgagta atgcgtgacc gacctgcccc      60
atacaccgga atagctcctg gaaacgggtg gtaatgccgg atgctccagt tgatcgcatg     120
gtcttctggg aaagctttcg cggtatggga tggggtcgcg tcctatcagc ttgacggcgg     180
ggtaacggcc caccgtggct tcgacgggta gccggcctga gagggcgacc ggccacattg     240
ggactgagat acgcccaga ctcctacggg aggcagcagt ggggaatatt gcacaatggg     300
cgcaagcctg atgcagcgac gccgcgtgag ggatggaggc cttcgggttg taaacctctt     360
ttatcgggga gcaagcgaga gtgagtttac ccgttgaata agcaccggct aactacgtgc     420
cagcagccgc ggtaatacgt agggtgcaag cgttatccgg aattattggg cgtaaagggc     480
tcgtaggcgg ttcgtcgcgt ccggtgtgaa agtccatcgc ttaacggtgg atccgcgccg     540
ggtacgggcg gcttgagtg cggtagggga gactggaatt cccggtgtaa cggtggaatg     600
tgtagatatc gggaagaaca ccaatggcga aggcaggtct ctgggccgtt actgacgctg     660
```

-continued

```
aggagcgaaa gcgtggggag cgaacaggat tagataccct ggtagtccac gccgtaaacg    720
gtggatgctg gatgtggggc ccgttccacg ggttccgtgt cggagctaac gcgttaagca    780
tcccgcctgg gggagtacgg ccgcaaggct aaaactcaaa gaaattgacg ggggcccgca    840
caagcggcgg agcatgcgga ttaattcgat gcaacgcgaa gaaccttacc tgggcttcac    900
atgttcccga cggtcgtaga gatacggctt cccttcgggg cgggttcaca ggtggtgcat    960
ggtcgtcgtc agctcgtgtc gtgagatgtt gggttaagtc ccgcaacgag cgcaaccctc   1020
gccccgtgtt gccagcggat tatgccggga actcacgggg gaccgccggg gttaactcgg   1080
aggaaggtgg ggatgacgtc agatcatcat gccccttacg tccagggctt cacgcatgct   1140
acaatggccg gtacaacggg atgcgacgcg gcgacgcgga gcggatccct gaaaaccggt   1200
ctcagttcgg atcgcagtct gcaactcgac tgcgtgaagg cggagtcgct agtaatcgcg   1260
aatcagcaac gtcgcggtga atgcgttccc gggccttgta cacaccgccc gtcaagtcat   1320
gaaagtgggc agcacccgaa gccggtgg                                      1348
```